US009782253B2

(12) United States Patent
Culbertson et al.

(10) Patent No.: US 9,782,253 B2
(45) Date of Patent: Oct. 10, 2017

(54) METHOD FOR PATTERNED PLASMA-MEDIATED MODIFICATION OF THE CRYSTALLINE LENS

(71) Applicant: Optimedica Corporation, Santa Ana, CA (US)

(72) Inventors: William Culbertson, Miami, FL (US); Barry Seibel, Pacific Palisades, CA (US); Neil Friedman, Menlo Park, CA (US); Georg Schuele, Menlo Park, CA (US); Phillip Gooding, Mountain View, CA (US)

(73) Assignee: Optimedica Corporation, Santa Ana, CA (US)

( * ) Notice: Subject to any disclaimer, the term of this patent is extended or adjusted under 35 U.S.C. 154(b) by 0 days.

(21) Appl. No.: 14/576,422

(22) Filed: Dec. 19, 2014

(65) Prior Publication Data
US 2015/0105762 A1    Apr. 16, 2015

Related U.S. Application Data

(62) Division of application No. 12/702,242, filed on Feb. 8, 2010, now Pat. No. 8,968,375, which is a division
(Continued)

(51) Int. Cl.
*A61B 19/00* (2006.01)
*A61F 2/16* (2006.01)
*A61F 9/008* (2006.01)

(52) U.S. Cl.
CPC ............. *A61F 2/1613* (2013.01); *A61F 2/16* (2013.01); *A61F 2/1637* (2013.01);
(Continued)

(58) Field of Classification Search
CPC ............ A61B 18/20; A61B 2018/2085; A61B 2018/2095; A61F 9/008
(Continued)

(56) References Cited

U.S. PATENT DOCUMENTS

| 4,169,664 A | 10/1979 | Bailey, Jr. |
| 4,309,998 A | 1/1982 | Aron et al. |

(Continued)

FOREIGN PATENT DOCUMENTS

| EP | 1279386 A1 | 1/2003 |
| EP | 1364632 A1 | 11/2003 |

(Continued)

OTHER PUBLICATIONS

Abstract of AU Publication No. 2007292491, Publication Date Mar. 13, 2008, which is the AU counterpart of the WO08030718 A2 application.

(Continued)

*Primary Examiner* — Ahmed Farah
(74) *Attorney, Agent, or Firm* — Abbot Medical Optics Inc.

(57) ABSTRACT

A method of treating a cataractous lens of a patient's eye includes generating a light beam, deflecting the light beam using a scanner to form a treatment pattern, delivering the treatment pattern to the lens of the patient's eye to create a plurality of cuts in the form two or more different incisions patterns within the lens to segment the lens tissue into a plurality of patterned pieces, and mechanically breaking the lens into a plurality of pieces along the cuts. A first incision pattern includes two or more crossing cut incision planes. A second incision pattern includes a plurality of laser incision each extending along a first length between a posterior and an anterior surface of the lens capsule.

16 Claims, 10 Drawing Sheets

Related U.S. Application Data of application No. 12/048,185, filed on Mar. 13, 2008, now abandoned.

(60) Provisional application No. 60/906,944, filed on Mar. 13, 2007.

(52) U.S. Cl.
CPC ........ *A61F 2/1648* (2013.01); *A61F 9/00825* (2013.01); *A61F 2002/1683* (2013.01); *A61F 2009/0087* (2013.01); *A61F 2009/0088* (2013.01); *A61F 2009/00859* (2013.01); *A61F 2009/00872* (2013.01); *A61F 2009/00887* (2013.01); *A61F 2009/00897* (2013.01)

(58) Field of Classification Search
USPC .......................................... 128/898; 606/4, 6
See application file for complete search history.

(56) References Cited

U.S. PATENT DOCUMENTS

| | | |
|---|---|---|
| 4,538,608 A | 9/1985 | L'Esperance, Jr. |
| 4,917,486 A | 4/1990 | Raven et al. |
| 4,995,715 A | 2/1991 | Cohen |
| 5,098,426 A | 3/1992 | Sklar et al. |
| 5,112,328 A | 5/1992 | Taboada et al. |
| 5,246,435 A | 9/1993 | Bille et al. |
| 5,257,988 A | 11/1993 | L'Esperance, Jr. |
| 5,336,217 A | 8/1994 | Buys et al. |
| 5,391,165 A | 2/1995 | Fountain et al. |
| 5,437,658 A | 8/1995 | Muller et al. |
| 5,439,462 A | 8/1995 | Bille et al. |
| 5,459,570 A | 10/1995 | Swanson et al. |
| 5,480,396 A | 1/1996 | Simon et al. |
| 5,493,109 A | 2/1996 | Wei et al. |
| 5,505,693 A | 4/1996 | MacKool |
| 5,520,679 A | 5/1996 | Lin |
| 5,702,441 A | 12/1997 | Zhou |
| 5,719,673 A | 2/1998 | Dorsel et al. |
| 5,720,894 A | 2/1998 | Neev et al. |
| 5,743,902 A | 4/1998 | Trost |
| 5,748,352 A | 5/1998 | Hattori |
| 5,748,898 A | 5/1998 | Ueda |
| 5,779,696 A | 7/1998 | Berry et al. |
| 5,865,830 A | 2/1999 | Parel et al. |
| 5,906,611 A | 5/1999 | Dodick et al. |
| 5,957,915 A | 9/1999 | Trost |
| 5,971,978 A | 10/1999 | Mukai |
| 5,980,513 A | 11/1999 | Frey et al. |
| 5,984,916 A | 11/1999 | Lai |
| 5,993,438 A | 11/1999 | Juhasz et al. |
| 6,002,127 A | 12/1999 | Vestal et al. |
| 6,004,314 A | 12/1999 | Wei et al. |
| 6,019,472 A | 2/2000 | Koester et al. |
| 6,053,613 A | 4/2000 | Wei et al. |
| 6,057,543 A | 5/2000 | Vestal et al. |
| 6,099,522 A | 8/2000 | Knopp et al. |
| 6,110,166 A | 8/2000 | Juhasz |
| 6,111,645 A | 8/2000 | Tearney et al. |
| 6,146,375 A | 11/2000 | Juhasz et al. |
| 6,149,644 A | 11/2000 | Xie |
| 6,210,401 B1 | 4/2001 | Lai |
| 6,254,595 B1 | 7/2001 | Juhasz et al. |
| 6,281,493 B1 | 8/2001 | Vestal et al. |
| 6,322,556 B1 | 11/2001 | Gwon et al. |
| 6,324,191 B1 | 11/2001 | Horvath |
| 6,325,792 B1 | 12/2001 | Swinger et al. |
| 6,328,733 B1 | 12/2001 | Trost |
| RE37,504 E | 1/2002 | Lin |
| 6,344,040 B1 | 2/2002 | Juhasz et al. |
| RE37,585 E | 3/2002 | Mourou et al. |
| 6,373,571 B1 | 4/2002 | Juhasz et al. |
| 6,396,587 B1 | 5/2002 | Knupfer et al. |
| D459,806 S | 7/2002 | Webb |
| D459,807 S | 7/2002 | Webb |
| D462,442 S | 9/2002 | Webb |
| D462,443 S | 9/2002 | Webb |
| 6,454,761 B1 | 9/2002 | Freedman |
| 6,497,701 B2 | 12/2002 | Shimmick et al. |
| 6,610,050 B2 | 8/2003 | Bille |
| 6,623,476 B2 | 9/2003 | Kurtz et al. |
| 6,638,271 B2 | 10/2003 | Munnerlyn et al. |
| 6,648,877 B1 | 11/2003 | Juhasz et al. |
| 6,652,511 B1 | 11/2003 | Tomita |
| 6,676,653 B2 | 1/2004 | Juhasz et al. |
| 6,693,927 B1 | 2/2004 | Horvath et al. |
| 6,706,036 B2 | 3/2004 | Lai |
| 6,751,033 B2 | 6/2004 | Goldstein et al. |
| 6,754,419 B2 | 6/2004 | Ide et al. |
| 6,902,561 B2 | 6/2005 | Kurtz et al. |
| 6,984,227 B2 | 1/2006 | Munnerlyn et al. |
| 7,027,233 B2 | 4/2006 | Goldstein et al. |
| 7,146,983 B1 | 12/2006 | Hohla et al. |
| 7,220,255 B2 | 5/2007 | Lai |
| 7,655,002 B2 | 2/2010 | Myers, I et al. |
| 7,662,148 B2 | 2/2010 | Kuhn et al. |
| 7,717,907 B2 | 5/2010 | Ruiz et al. |
| 7,766,903 B2 | 8/2010 | Blumenkranz et al. |
| 7,994,307 B2 | 8/2011 | Hadwiger et al. |
| 8,186,357 B2 | 5/2012 | Lubatschowski et al. |
| 8,262,646 B2 | 9/2012 | Frey et al. |
| 8,350,183 B2 | 1/2013 | Vogel et al. |
| 8,382,745 B2 | 2/2013 | Naranjo-Tackman et al. |
| 8,394,084 B2 * | 3/2013 | Palankar et al. .................. 606/6 |
| 8,414,564 B2 | 4/2013 | Goldshleger et al. |
| 8,690,862 B2 * | 4/2014 | Palanker ............. A61F 9/00736 606/2 |
| 2002/0103478 A1 | 8/2002 | Gwon et al. |
| 2002/0128637 A1 | 9/2002 | Von Der Heide et al. |
| 2003/0053219 A1 | 3/2003 | Manzi |
| 2003/0060880 A1 | 3/2003 | Feingold |
| 2004/0148022 A1 | 7/2004 | Eggleston |
| 2004/0243112 A1 | 12/2004 | Bendett et al. |
| 2006/0235428 A1 | 10/2006 | Silvestrini |
| 2007/0173794 A1 * | 7/2007 | Frey ......................... A61F 9/008 606/5 |
| 2007/0173795 A1 | 7/2007 | Frey et al. |
| 2008/0058841 A1 | 3/2008 | Kurtz et al. |
| 2008/0281303 A1 | 11/2008 | Culbertson et al. |
| 2008/0281413 A1 | 11/2008 | Culbertson et al. |
| 2010/0137850 A1 | 6/2010 | Culbertson et al. |
| 2010/0137982 A1 | 6/2010 | Culbertson et al. |
| 2010/0137983 A1 | 6/2010 | Culbertson et al. |
| 2010/0191226 A1 | 7/2010 | Blumenkranz et al. |
| 2011/0319873 A1 | 12/2011 | Raksi et al. |
| 2011/0319875 A1 | 12/2011 | Loesel et al. |
| 2014/0378955 A1 * | 12/2014 | Gray .................. A61F 9/00827 606/5 |
| 2015/0105763 A1 * | 4/2015 | Culbertson ............... A61F 2/16 606/6 |
| 2015/0230987 A1 * | 8/2015 | Friedman ............ A61F 9/00825 606/6 |

FOREIGN PATENT DOCUMENTS

| | | |
|---|---|---|
| WO | 9308877 A1 | 5/1993 |
| WO | 9407424 A1 | 4/1994 |
| WO | 2008030718 A2 | 3/2008 |

OTHER PUBLICATIONS

Baikoff G., et al., "Contact Between 3 Phakic Intraocular Lens Models and the Crystalline Lens: An Anterior Chamber Optical Coherence Tomography Study," Journal of Cataract and Refractive Surgery, 2004, vol. 30 (9), pp. 2007-2012.

Geerling G., et al., "Initial Clinical Experience with the Picosecond Nd:YLF Laser for Intraocular Therapeutic Applications," British Journal of Ophthalmology, 1998, vol. 82 (5), pp. 504-509.

Gimbel H.V., et al., "Continuous Curvilinear Capsulorhexis," Journal of Cataract and Refractive Surgery, 1991, vol. 17 (1), pp. 110-111.

(56) References Cited

OTHER PUBLICATIONS

Gimbel H.V., et al., "Development, Advantages and Methods of the Continuous Circular Capsulorhexis Technique," Journal of Cataract and Refractive Surgery, 1990, vol. 16 (1), pp. 31-37.
Gimbel H.V., et al., "Principles of Nuclear Phaco Emulsification" In: Cataract Surgery Techniques Complications and Management, 2nd edition., Steinert et al., 2004, Chap. 15, pp. 153-181.
Izatt J.A., et al., "Micrometer-Scale Resolution Imaging of the Anterior Eye In Vivo With Optical Coherence Tomography," Arch Ophthalmology, 1994, vol. 112 (12), pp. 1584-1589.
Steinert et al., "Neodymium: Yttrium-Aluminum-Garnet Laser Posterior Capsulotomy," in: Cataract Surgery Techniques Complications and Management, 2nd edition., Steinert et al., 2004, Chapter. 44, pp. 531-544.
Supplementary European Search Report for Application No. EP08726822, mailed on Apr. 9, 2010, 6 pages.
Supplementary European Search Report for Application No. EP08726825, mailed on Apr. 30, 2010, 8 pages.

* cited by examiner

METHOD FOR PATTERNED PLASMA-MEDIATED MODIFICATION OF THE CRYSTALLINE LENS

RELATED APPLICATIONS

This application is a divisional of U.S. patent application Ser. No. 12/702,242, filed Feb. 8, 2010, which is a divisional of U.S. patent application Ser. No. 12/048,185, filed Mar. 13, 2008, now abandoned, which claims the benefit of U.S. Provisional application No. 60/906,944, filed Mar. 13, 2007, the entire contents of all of which are incorporated herein by reference in their entirety.

FIELD OF THE INVENTION

The present invention relates to ophthalmic surgical procedures and systems.

BACKGROUND OF THE INVENTION

Cataract extraction is one of the most commonly performed surgical procedures in the world with estimated 2.5 million cases performed annually in the United States and 9.1 million cases worldwide in 2000. This was expected to increase to approximately 13.3 million estimated global cases in 2006. This market is composed of various segments including intraocular lenses for implantation, viscoelastic polymers to facilitate surgical maneuvers, disposable instrumentation including ultrasonic phacoemulsification tips, tubing, and various knives and forceps. Modern cataract surgery is typically performed using a technique termed phacoemulsification in which an ultrasonic tip with an associated water stream for cooling purposes is used to sculpt the relatively hard nucleus of the lens after performance of an opening in the anterior lens capsule termed anterior capsulotomy or more recently capsulorhexis. Following these steps as well as removal of residual softer lens cortex by aspiration methods without fragmentation, a synthetic foldable intraocular lens (IOL) is inserted into the eye through a small incision.

One of the earliest and most critical steps in the procedure is the performance of capsulorhexis. This step evolved from an earlier technique termed can-opener capsulotomy in which a sharp needle was used to perforate the anterior lens capsule in a circular fashion followed by the removal of a circular fragment of lens capsule typically in the range of 5-8 mm in diameter. This facilitated the next step of nuclear sculpting by phacoemulsification. Due to a variety of complications associated with the initial can-opener technique, attempts were made by leading experts in the field to develop a better technique for removal of the anterior lens capsule preceding the emulsification step. The concept of the Continuous Curvilinear Capsulorhexis (CCC) is to provide a smooth continuous circular opening through which not only the phacoemulsification of the nucleus can be performed safely and easily, but also for easy insertion of the intraocular lens. It provides both a clear central access for insertion, a permanent aperture for transmission of the image to the retina by the patient, and also a support of the IOL inside the remaining capsule that would limit the potential for dislocation. Subsequent to the step of anterior CCC, and prior to IOL insertion the steps of hydrodissection, hydrodilineation and phaco emulsification occur. These are intended to identify and soften the nucleus for the purposes of removal from the eye. These are the longest and thought to be the most dangerous step in the procedure due to the mechanical manipulation and the use of pulses of ultrasound that may lead to inadvertent ruptures of the posterior lens capsule, posterior dislocation of lens fragments, and potential damage anteriorly to the corneal endothelium and/or iris and other delicate intraocular structures. The central nucleus of the lens, which undergoes the most opacification and thereby the most visual impairment, is structurally the hardest and requires special techniques. A variety of surgical maneuvers employing ultrasonic fragmentation and also requiring considerable technical dexterity on the part of the surgeon have evolved, including sculpting, cracking and chopping of the lens, the so-called "divide and conquer technique" and a whole host of similarly creatively named techniques, such as phaco chop, etc. These are all subject to the usual complications associated with delicate intraocular maneuvers.

What is needed are ophthalmic methods, techniques and apparatus to advance the standard of care of cataract and other ophthalmic pathologies.

SUMMARY OF THE INVENTION

The aforementioned problems and needs are addressed by providing a method of treating a lens of a patient using various scanned patterns of optical energy to soften and/or segment the lens for removal.

A method of treating a lens of a patient's eye includes generating a light beam, deflecting the light beam using a scanner to form a treatment pattern of the light beam, delivering the treatment pattern to the lens of a patient's eye to create a plurality of cuts in the lens in the form of the treatment pattern, mechanically breaking the lens into a plurality of pieces along the cuts, and removing the lens pieces from the patient's eye.

Other objects and features of the present invention will become apparent by a review of the specification, claims and appended figures.

DETAILED DESCRIPTION OF THE PREFERRED EMBODIMENTS

Figure 1:
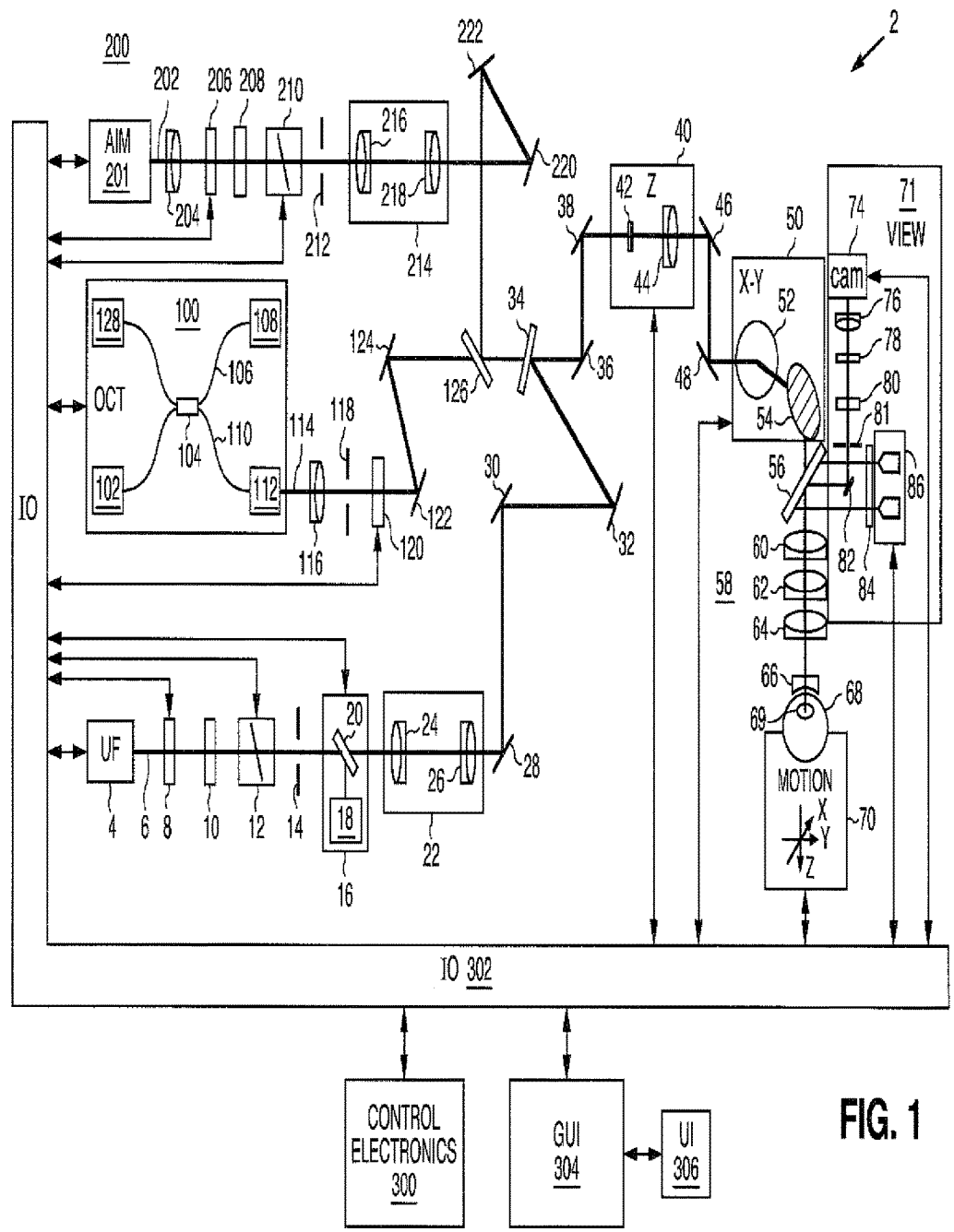
FIG. 1 is a schematic diagram of the optical beam scanning system.

The present invention can be implemented by a system that projects or scans an optical beam into a patient's eye 68, such as system 2 shown in FIG. 1 which includes an ultrafast (UF) light source 4 (e.g. a femtosecond laser). Using this system, a beam may be scanned in a patient's eye in three dimensions: X, Y, Z. In this embodiment, the UF wavelength can vary between 1010 nm to 1100 nm and the pulse width can vary from 100 fs to 10000 fs. The pulse repetition frequency can also vary from 10 kHz to 250 kHz. Safety limits with regard to unintended damage to non-targeted tissue bound the upper limit with regard to repetition rate and pulse energy; while threshold energy, time to complete the procedure and stability bound the lower limit for pulse energy and repetition rate. The peak power of the focused spot in the eye 68 and specifically within the crystalline lens 69 and anterior capsule of the eye is sufficient to produce optical breakdown and initiate a plasma-mediated ablation process. Near-infrared wavelengths are preferred because linear optical absorption and scattering in biological tissue is reduced across that spectral range. As an example, laser 4 may be a repetitively pulsed 1035 nm device that produces 500 fs pulses at a repetition rate of 100 kHz and an individual pulse energy in the ten microjoule range.

The laser 4 is controlled by control electronics 300, via an input and output device 302, to create optical beam 6. Control electronics 300 may be a computer, microcontroller, etc. In this example, the entire system is controlled by the controller 300, and data moved through input/output device IO 302. A graphical user interface GUI 304 may be used to set system operating parameters, process user input (UI) 306 on the GUI 304, and display gathered information such as images of ocular structures.

The generated UF light beam 6 proceeds towards the patient eye 68 passing through half-wave plate, 8, and linear polarizer, 10. The polarization state of the beam can be adjusted so that the desired amount of light passes through half-wave plate 8 and linear polarizer 10, which together act as a variable attenuator for the UF beam 6. Additionally, the orientation of linear polarizer 10 determines the incident polarization state incident upon beamcombiner 34, thereby optimizing beamcombiner throughput.

The UF beam proceeds through a shutter 12, aperture 14, and a pickoff device 16. The system controlled shutter 12 ensures on/off control of the laser for procedural and safety reasons. The aperture sets an outer useful diameter for the laser beam and the pickoff monitors the output of the useful beam. The pickoff device 16 includes of a partially reflecting mirror 20 and a detector 18. Pulse energy, average power, or a combination may be measured using detector 18. The information can be used for feedback to the half-wave plate 8 for attenuation and to verify whether the shutter 12 is open or closed. In addition, the shutter 12 may have position sensors to provide a redundant state detection.

The beam passes through a beam conditioning stage 22, in which beam parameters such as beam diameter, divergence, circularity, and astigmatism can be modified. In this illustrative example, the beam conditioning stage 22 includes a 2 element beam expanding telescope comprised of spherical optics 24 and 26 in order to achieve the intended beam size and collimation. Although not illustrated here, an anamorphic or other optical system can be used to achieve the desired beam parameters. The factors used to determine these beam parameters include the output beam parameters of the laser, the overall magnification of the system, and the desired numerical aperture (NA) at the treatment location. In addition, the optical system 22 can be used to image aperture 14 to a desired location (e.g. the center location between the 2-axis scanning device 50 described below). In this way, the amount of light that makes it through the aperture 14 is assured to make it through the scanning system. Pickoff device 16 is then a reliable measure of the usable light.

After exiting conditioning stage 22, beam 6 reflects off of fold mirrors 28, 30, & 32. These mirrors can be adjustable for alignment purposes. The beam 6 is then incident upon beam combiner 34. Beamcombiner 34 reflects the UF beam 6 (and transmits both the OCT 114 and aim 202 beams described below). For efficient beamcombiner operation, the angle of incidence is preferably kept below 45 degrees and the polarization where possible of the beams is fixed. For the UF beam 6, the orientation of linear polarizer 10 provides fixed polarization.

Following the beam combiner 34, the beam 6 continues onto the z-adjust or Z scan device 40. In this illustrative example the z-adjust includes a Galilean telescope with two lens groups 42 and 44 (each lens group includes one or more lenses). Lens group 42 moves along the z-axis about the collimation position of the telescope. In this way, the focus position of the spot in the patient's eye 68 moves along the z-axis as indicated. In general there is a fixed linear relationship between the motion of lens 42 and the motion of the focus. In this case, the z-adjust telescope has an approximate 2× beam expansion ratio and a 1:1 relationship of the movement of lens 42 to the movement of the focus. Alternatively, lens group 44 could be moved along the z-axis to actuate the z-adjust, and scan. The z-adjust is the z-scan device for treatment in the eye 68. It can be controlled automatically and dynamically by the system and selected to be independent or to interplay with the X-Y scan device described next. Mirrors 36 and 38 can be used for aligning the optical axis with the axis of z-adjust device 40.

After passing through the z-adjust device 40, the beam 6 is directed to the x-y scan device by mirrors 46 & 48. Mirrors 46 & 48 can be adjustable for alignment purposes. X-Y scanning is achieved by the scanning device 50 preferably using two mirrors 52 & 54 under the control of control electronics 300, which rotate in orthogonal directions using motors, galvanometers, or any other well known optic moving device. Mirrors 52 & 54 are located near the telecentric position of the objective lens 58 and contact lens 66 combination described below. Tilting these mirrors 52/54 causes them to deflect beam 6, causing lateral displacements in the plane of UF focus located in the patient's eye 68. Objective lens 58 may be a complex multi-element lens element, as shown, and represented by lenses 60, 62, and 64. The complexity of the lens 58 will be dictated by the scan field size, the focused spot size, the available working distance on both the proximal and distal sides of objective 58, as well as the amount of aberration control. An f-theta lens 58 of focal length 60 mm generating a spot size of 10 µm, over a field of 10 mm, with an input beam size of 15 mm diameter is an example. Alternatively, X-Y scanning by scanner 50 may be achieved by using one or more moveable optical elements (e.g. lenses, gratings) which also may be controlled by control electronics 300, via input and output device 302.

The aiming and treatment scan patterns can be automatically generated by the scanner 50 under the control of controller 300. Such patterns may be comprised of a single spot of light, multiple spots of light, a continuous pattern of light, multiple continuous patterns of light, and/or any combination of these. In addition, the aiming pattern (using aim beam 202 described below) need not be identical to the treatment pattern (using light beam 6), but preferably at least defines its boundaries in order to assure that the treatment light is delivered only within the desired target area for patient safety. This may be done, for example, by having the aiming pattern provide an outline of the intended treatment pattern. This way the spatial extent of the treatment pattern may be made known to the user, if not the exact locations of the individual spots themselves, and the scanning thus optimized for speed, efficiency and accuracy. The aiming pattern may also be made to be perceived as blinking in order to further enhance its visibility to the user.

An optional contact lens 66, which can be any suitable ophthalmic lens, can be used to help further focus the optical beam 6 into the patient's eye 68 while helping to stabilize eye position. The positioning and character of optical beam 6 and/or the scan pattern the beam 6 forms on the eye 68 may be further controlled by use of an input device such as a joystick, or any other appropriate user input device (e.g. GUI 304) to position the patient and/or the optical system.

The UF laser 4 and controller 300 can be set to target the surfaces of the targeted structures in the eye 68 and ensure that the beam 6 will be focused where appropriate and not unintentionally damage non-targeted tissue. Imaging modalities and techniques described herein, such as for example, Optical Coherence Tomography (OCT), Purkinje imaging, Scheimpflug imaging, or ultrasound may be used to determine the location and measure the thickness of the lens and lens capsule to provide greater precision to the laser focusing methods, including 2D and 3D patterning. Laser focusing may also be accomplished using one or more methods including direct observation of an aiming beam, Optical Coherence Tomography (OCT), Purkinje imaging, Scheimpflug imaging, ultrasound, or other known ophthalmic or medical imaging modalities and/or combinations thereof. In the embodiment of FIG. 1, an OCT device 100 is described, although other modalities are within the scope of the present invention. An OCT scan of the eye will provide information about the axial location of the anterior and posterior lens capsule, the boundaries of the cataract nucleus, as well as the depth of the anterior chamber. This information is then be loaded into the control electronics 300, and used to program and control the subsequent laser-assisted surgical procedure. The information may also be used to determine a wide variety of parameters related to the procedure such as, for example, the upper and lower axial limits of the focal planes used for cutting the lens capsule and segmentation of the lens cortex and nucleus, and the thickness of the lens capsule among others.

The OCT device 100 in FIG. 1 includes a broadband or a swept light source 102 that is split by a fiber coupler 104 into a reference arm 106 and a sample arm 110. The reference arm 106 includes a module 108 containing a reference reflection along with suitable dispersion and path length compensation. The sample arm 110 of the OCT device 100 has an output connector 112 that serves as an interface to the rest of the UF laser system. The return signals from both the reference and sample arms 106, 110 are then directed by coupler 104 to a detection device 128, which employs either time domain, frequency or single point detection techniques. In FIG. 1, a frequency domain technique is used with an OCT wavelength of 920 nm and bandwidth of 100 nm.

Exiting connector 112, the OCT beam 114 is collimated using lens 116. The size of the collimated beam 114 is determined by the focal length of lens 116. The size of the beam 114 is dictated by the desired NA at the focus in the eye and the magnification of the beam train leading to the eye 68. Generally, OCT beam 114 does not require as high an NA as the UF beam 6 in the focal plane and therefore the OCT beam 114 is smaller in diameter than the UF beam 6 at the beamcombiner 34 location. Following collimating lens 116 is aperture 118 which further modifies the resultant NA of the OCT beam 114 at the eye. The diameter of aperture 118 is chosen to optimize OCT light incident on the target tissue and the strength of the return signal. Polarization control element 120, which may be active or dynamic, is used to compensate for polarization state changes which may be induced by individual differences in corneal birefringence, for example. Mirrors 122 & 124 are then used to direct the OCT beam 114 towards beamcombiners 126 & 34. Mirrors 122 & 124 may be adjustable for alignment purposes and in particular for overlaying of OCT beam 114 to UF beam 6 subsequent to beamcombiner 34. Similarly, beamcombiner 126 is used to combine the OCT beam 114 with the aim beam 202 described below.

Once combined with the UF beam 6 subsequent to beamcombiner 34, OCT beam 114 follows the same path as UF beam 6 through the rest of the system. In this way, OCT beam 114 is indicative of the location of UF beam 6. OCT beam 114 passes through the z-scan 40 and x-y scan 50 devices then the objective lens 58, contact lens 66 and on into the eye 68. Reflections and scatter off of structures within the eye provide return beams that retrace back through the optical system, into connector 112, through coupler 104, and to OCT detector 128. These return back reflections provide the OCT signals that are in turn interpreted by the system as to the location in X, Y Z of UF beam 6 focal location.

OCT device 100 works on the principle of measuring differences in optical path length between its reference and sample arms. Therefore, passing the OCT through z-adjust 40 does not extend the z-range of OCT system 100 because the optical path length does not change as a function of movement of 42. OCT system 100 has an inherent z-range that is related to the detection scheme, and in the case of frequency domain detection it is specifically related to the spectrometer and the location of the reference arm 106. In the case of OCT system 100 used in FIG. 1, the z-range is approximately 1-2 mm in an aqueous environment. Extending this range to at least 4 mm involves the adjustment of the path length of the reference arm within OCT system 100. Passing the OCT beam 114 in the sample arm through the z-scan of z-adjust 40 allows for optimization of the OCT signal strength. This is accomplished by focusing the OCT beam 114 onto the targeted structure while accommodating the extended optical path length by commensurately increasing the path within the reference arm 106 of OCT system 100.

Because of the fundamental differences in the OCT measurement with respect to the UF focus device due to influences such as immersion index, refraction, and aberration, both chromatic and monochromatic, care must be taken in analyzing the OCT signal with respect to the UF beam focal location. A calibration or registration procedure as a function of X, Y Z should be conducted in order to match the OCT signal information to the UF focus location and also to the relate to absolute dimensional quantities.

Observation of an aim beam may also be used to assist the user to directing the UF laser focus. Additionally, an aim beam visible to the unaided eye in lieu of the infrared OCT and UF beams can be helpful with alignment provided the aim beam accurately represents the infrared beam parameters. An aim subsystem 200 is employed in the configuration shown in FIG. 1. The aim beam 202 is generated by a an aim beam light source 201, such as a helium-neon laser operating at a wavelength of 633 nm. Alternatively a laser diode in the 630-650 nm range could be used. The advantage of using the helium neon 633 nm beam is its long coherence length, which would enable the use of the aim path as a laser unequal path interferometer (LUPI) to measure the optical quality of the beam train, for example.

Once the aim beam light source generates aim beam 202, the aim beam 202 is collimated using lens 204. The size of the collimated beam is determined by the focal length of lens 204. The size of the aim beam 202 is dictated by the desired NA at the focus in the eye and the magnification of the beam train leading to the eye 68. Generally, aim beam 202 should have close to the same NA as UF beam 6 in the focal plane and therefore aim beam 202 is of similar diameter to the UF beam at the beamcombiner 34 location. Because the aim beam is meant to stand-in for the UF beam 6 during system alignment to the target tissue of the eye, much of the aim path mimics the UF path as described previously. The aim beam 202 proceeds through a half-wave plate 206 and linear polarizer 208. The polarization state of the aim beam 202 can be adjusted so that the desired amount of light passes through polarizer 208. Elements 206 & 208 therefore act as a variable attenuator for the aim beam 202. Additionally, the orientation of polarizer 208 determines the incident polarization state incident upon beamcombiners 126 and 34, thereby fixing the polarization state and allowing for optimization of the beamcombiners' throughput. Of course, if a semiconductor laser is used as aim beam light source 200, the drive current can be varied to adjust the optical power.

The aim beam 202 proceeds through a shutter 210 and aperture 212. The system controlled shutter 210 provides on/off control of the aim beam 202. The aperture 212 sets an outer useful diameter for the aim beam 202 and can be adjusted appropriately. A calibration procedure measuring the output of the aim beam 202 at the eye can be used to set the attenuation of aim beam 202 via control of polarizer 206.

The aim beam 202 next passes through a beam conditioning device 214. Beam parameters such as beam diameter, divergence, circularity, and astigmatism can be modified using one or more well known beaming conditioning optical elements. In the case of an aim beam 202 emerging from an optical fiber, the beam conditioning device 214 can simply include a beam expanding telescope with two optical elements 216 and 218 in order to achieve the intended beam size and collimation. The final factors used to determine the aim beam parameters such as degree of collimation are dictated by what is necessary to match the UF beam 6 and aim beam 202 at the location of the eye 68. Chromatic differences can be taken into account by appropriate adjustments of beam conditioning device 214. In addition, the optical system 214 is used to image aperture 212 to a desired location such as a conjugate location of aperture 14.

The aim beam 202 next reflects off of fold mirrors 222 & 220, which are preferably adjustable for alignment registration to UF beam 6 subsequent to beam combiner 34. The aim beam 202 is then incident upon beam combiner 126 where the aim beam 202 is combined with OCT beam 114. Beamcombiner 126 reflects the aim beam 202 and transmits the OCT beam 114, which allows for efficient operation of the beamcombining functions at both wavelength ranges. Alternatively, the transmit and reflect functions of beamcombiner 126 can be reversed and the configuration inverted. Subsequent to beamcombiner 126, aim beam 202 along with OCT beam 114 is combined with UF beam 6 by beamcombiner 34.

A device for imaging the target tissue on or within the eye 68 is shown schematically in FIG. 1 as imaging system 71. Imaging system includes a camera 74 and an illumination light source 86 for creating an image of the target tissue. The imaging system 71 gathers images which may be used by the system controller 300 for providing pattern centering about or within a predefined structure. The illumination light source 86 for the viewing is generally broadband and incoherent. For example, light source 86 can include multiple LEDs as shown. The wavelength of the viewing light source 86 is preferably in the range of 700 nm to 750 nm, but can be anything which is accommodated by the beamcombiner 56, which combines the viewing light with the beam path for UF beam 6 and aim beam 202 (beamcombiner 56 reflects the viewing wavelengths while transmitting the OCT and UF wavelengths). The beamcombiner 56 may partially transmit the aim wavelength so that the aim beam 202 can be visible to the viewing camera 74. Optional polarization element 84 in front of light source 86 can be a linear polarizer, a quarter wave plate, a half-wave plate or any combination, and is used to optimize signal. A false color image as generated by the near infrared wavelength is acceptable.

The illumination light from light source 86 is directed down towards the eye using the same objective lens 58 and contact lens 66 as the UF and aim beam 6, 202. The light reflected and scattered off of various structures in the eye 68 are collected by the same lenses 58 & 66 and directed back towards beamcombiner 56. There, the return light is directed back into the viewing path via beam combiner and mirror 82, and on to camera 74. Camera 74 can be, for example but not limited to, any silicon based detector array of the appropriately sized format. Video lens 76 forms an image onto the camera's detector array while optical elements 80 & 78 provide polarization control and wavelength filtering respectively. Aperture or iris 81 provides control of imaging NA and therefore depth of focus and depth of field. A small aperture provides the advantage of large depth of field which aids in the patient docking procedure. Alternatively, the illumination and camera paths can be switched. Furthermore, aim light source 200 can be made to emit in the infrared which would not directly visible, but could be captured and displayed using imaging system 71.

Coarse adjust registration is usually needed so that when the contact lens 66 comes into contact with the cornea, the targeted structures are in the capture range of the X, Y scan of the system. Therefore a docking procedure is preferred, which preferably takes in account patient motion as the system approaches the contact condition (i.e. contact between the patient's eye 68 and the contact lens 66. The viewing system 71 is configured so that the depth of focus is large enough such that the patient's eye 68 and other salient features may be seen before the contact lens 66 makes contact with eye 68.

Preferably, a motion control system 70 is integrated into the overall control system 2, and may move the patient, the system 2 or elements thereof, or both, to achieve accurate and reliable contact between contact lens 66 and eye 68. Furthermore, a vacuum suction subsystem and flange may be incorporated into system 2, and used to stabilize eye 68. The alignment of eye 68 to system 2 via contact lens 66 may be accomplished while monitoring the output of imaging system 71, and performed manually or automatically by analyzing the images produced by imaging system 71 electronically by means of control electronics 300 via IO 302. Force and/or pressure sensor feedback may also be used to discern contact, as well as to initiate the vacuum subsystem.

Figure 2:
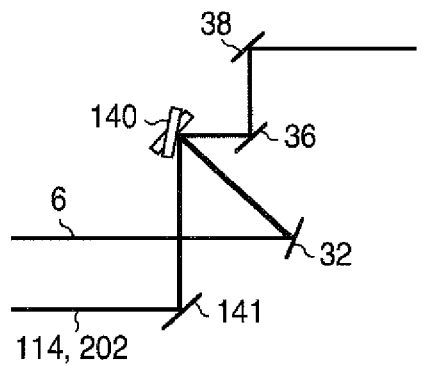
FIG. 2 is an optical diagram showing an alternative beam combining scheme.

An alternative beamcombining configuration is shown in the alternate embodiment of FIG. 2. For example, the passive beamcombiner 34 in FIG. 1 can be replaced with an active combiner 140 in FIG. 2. The active beamcombiner 34 can be a moving or dynamically controlled element such as a galvanometric scanning mirror, as shown. Active combiner 140 changes it angular orientation in order to direct either the UF beam 6 or the combined aim and OCT beams 202, 114 towards the scanner 50 and eventually eye 68 one at a time. The advantage of the active combining technique is that it avoids the difficulty of combining beams with similar wavelength ranges or polarization states using a passive beam combiner. This ability is traded off against the ability to have simultaneous beams in time and potentially less accuracy and precision due to positional tolerances of active beam combiner 140.

Figure 3:
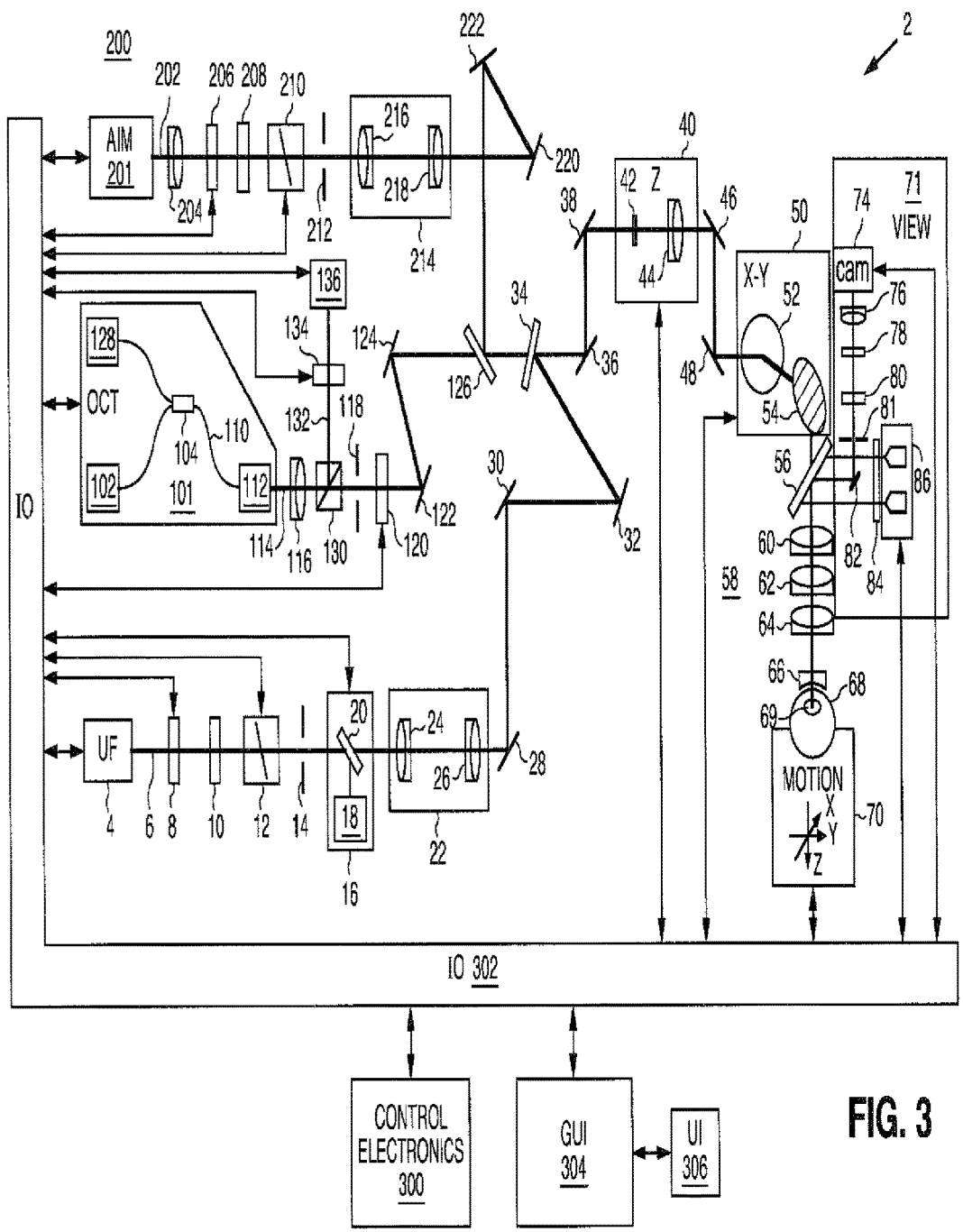
FIG. 3 is a schematic diagram of the optical beam scanning system with an alternative OCT configuration.

Another alternate embodiment is shown in FIG. 3 which is similar to that of FIG. 1 but utilizes an alternate approach to OCT 100. In FIG. 3, OCT 101 is the same as OCT 100 in FIG. 1, except that the reference arm 106 has been replaced by reference arm 132. This free-space OCT reference arm 132 is realized by including beamsplitter 130 after lens 116. The reference beam 132 then proceeds through polarization controlling element 134 and then onto the reference return module 136. The reference return module 136 contains the appropriate dispersion and path length adjusting and compensating elements and generates an appropriate reference signal for interference with the sample signal. The sample arm of OCT 101 now originates subsequent to beamsplitter 130. The potential advantages of this free space configuration include separate polarization control and maintenance of the reference and sample arms. The fiber based beam splitter 104 of OCT 101 can also be replaced by a fiber based circulator. Alternately, both OCT detector 128 and beamsplitter 130 might be moved together as opposed to reference arm 136.

Figure 4:
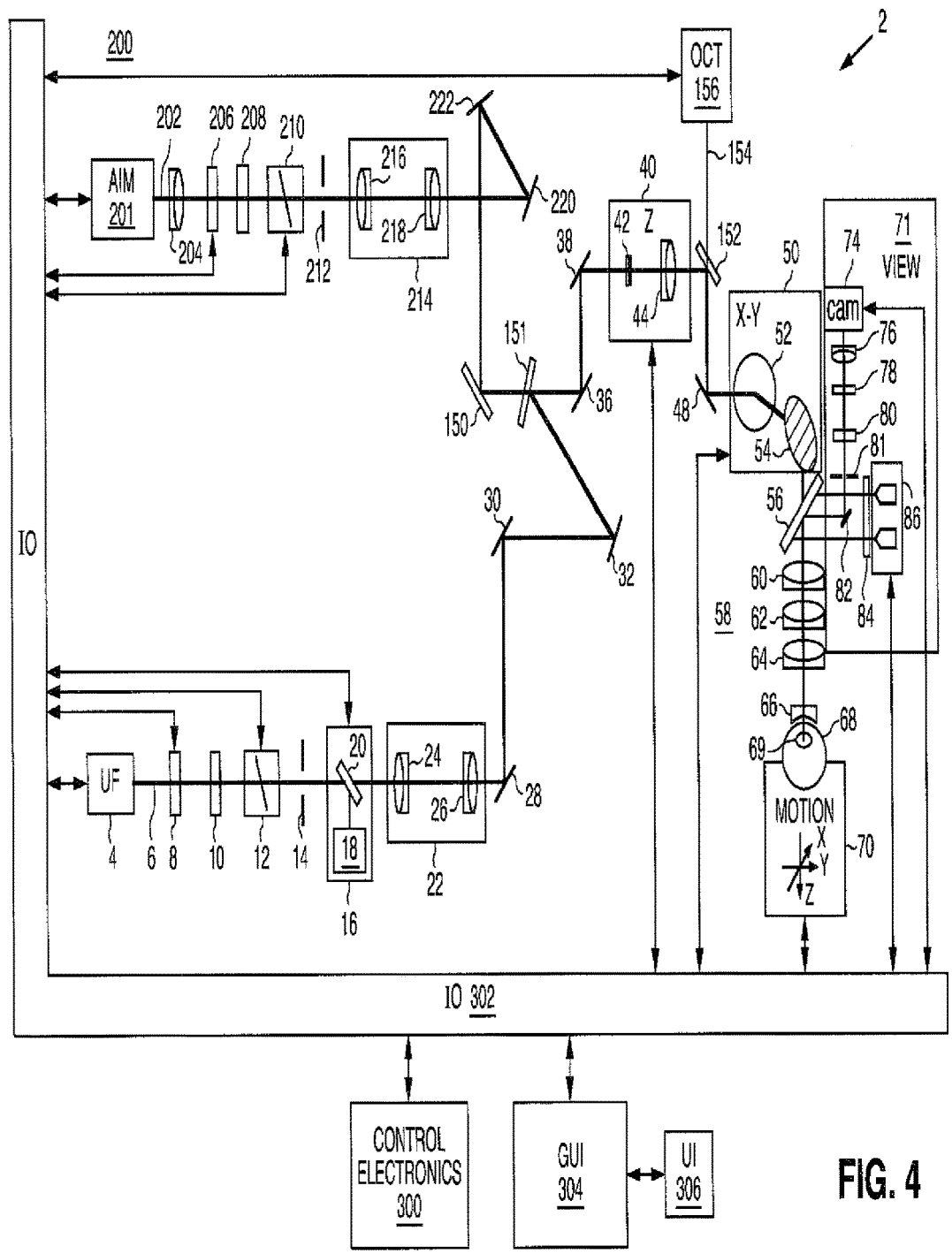
FIG. 4 is a schematic diagram of the optical beam scanning system with another alternative OCT combining scheme.

FIG. 4 shows another alternative embodiment for combining OCT beam 114 and UF beam 6. In FIG. 4, OCT 156 (which can include either of the configurations of OCT 100 or 101) is configured such that its OCT beam 154 is coupled to UF beam 6 after the z-scan 40 using beamcombiner 152. In this way, OCT beam 154 avoids using the z-adjust. This allows the OCT 156 to possibly be folded into the beam more easily and shortening the path length for more stable operation. This OCT configuration is at the expense of an optimized signal return strength as discussed with respect to FIG. 1. There are many possibilities for the configuration of the OCT interferometer, including time and frequency domain approaches, single and dual beam methods, swept source, etc, as described in U.S. Pat. Nos. 5,748,898; 5,748,352; 5,459,570; 6,111,645; and 6,053,613 (which are incorporated herein by reference.)

FIGS. 5 through 15 illustrate the various embodiments of the present invention. Specifically, they describe possible scanned 3-dimensional patterns within lens 69 of the patient's eye 68. These patterns have been specifically designed to provide more convenient splitting of lens 69 into segments that are easy to aspirate using existing technology and devices. Phacoemulsification is particularly well suited for this. Several such aspiration devices are commercially available and well known in the art.

Figure 5A:
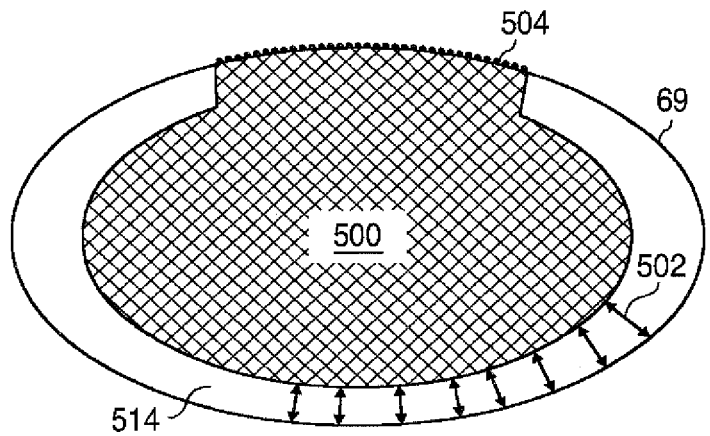
FIGS. 5A-5C are side cross sectional views of the lens of the eye illustrating various treatment zones.
Figure 5B:
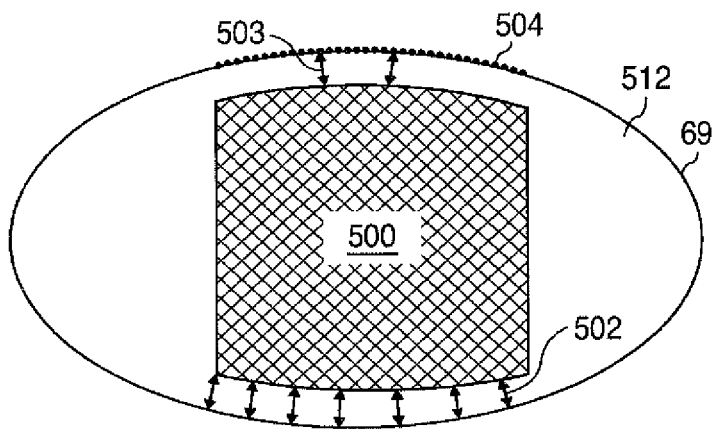
Figure 5C:
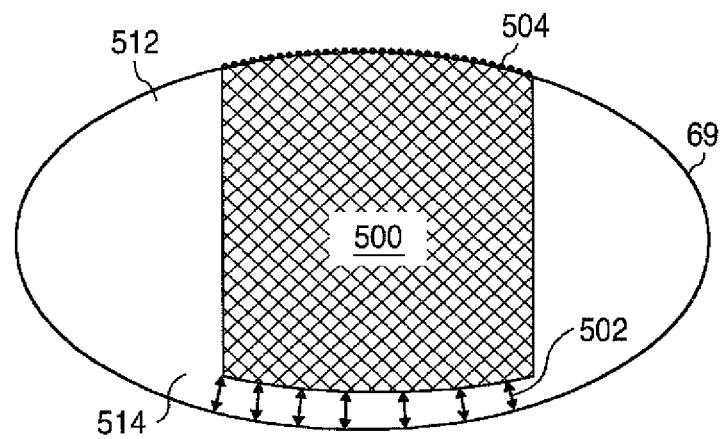

FIG. 5A to 5C illustrate a side views of lens 69 and the depth profiles of the patterns of FIGS. 6 to 15. Specifically, in FIGS. 5A to 5C, treatment zone 500 denotes the internal volume of lens 69 where beam 6 is used for softening the cataractous material within lens 69. Treatment zone 500 has a high density of laser exposures, but a distinct safety zone 502 in the lens 69 between the treatment zone 500 and the posterior capsular bag surface 514 is preferably maintained, to insure that the surface 514 is not damaged by beam 6. The inner boundary of safety zone 502 ranges between 10 µm to 1000 µm away from surface 514, but is typically 30 µm, and may be determined by use of OCT device 100 within system 2. Safety zone 502 may also comprise the softer portions of lens 69, the cortex and epi-nucleus. Safety zone 502 may also be a function of the numerical aperture (NA) used for beams 6, 114 & 202 in system. 2. The higher the NA used, the closer the focus of beam 6 from system 2 can be to surface 514 without risk of incidental damage due to the increased divergence of beam 6. Damage to posterior surface 514 may cause surgical complications, and retinal damage.

As shown in FIG. 5A, safety zone 502 is maintained throughout lens 69 except opening 504 in anterior surface 512 of the capsule, as that portion of the capsule will ultimately be removed.

FIG. 5B shows the example where treatment zone 500 extends in a cylindrical shape of circular projection from the front (top) of lens 69, with the addition of safety zone 503 adjacent to surface 512 in addition to safety zone 502 for posterior surface 514.

FIG. 5C shows an alternate embodiment where treatment zone 500 extends in a cylindrical shape and only safety zone 502 is used. This represents the case where area 504 of anterior surface 512 will be incised and ultimately removed, so safety zone 503 is not required.

In both FIGS. 5B and 5C, the diameter of the cylindrical treatment zone 500 can be the same size as the capsular opening but also smaller or bigger than capsular opening 504. The safety zone 502 is used for "lens-in-the-bag" IOL implants. In the alternate case of a "bag-in-the-lens" approach, where the posterior capsule will also be incised and ultimately removed, incisions will be made by the system in posterior surface 514 and the safety zone 502 need not be used, similarly to the case of FIG. 5C.

Figure 6A:
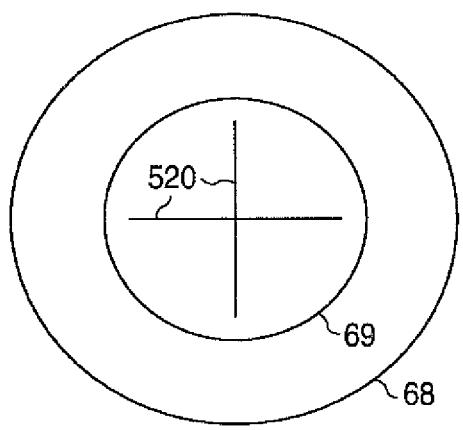
FIGS. 6A-6C are top views of an eye lens illustrating various configurations of line cuts.
Figure 6B:
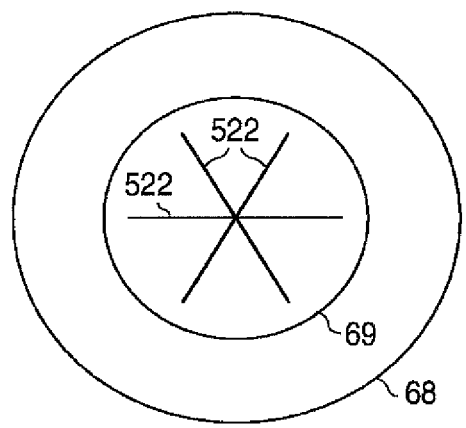
Figure 6C:
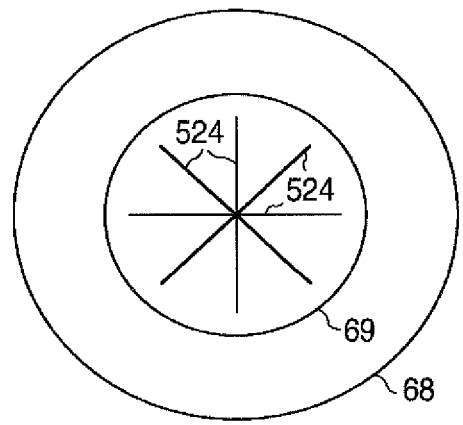

In nearly all previously described ultrasonic phacoemulsification techniques, lens 69 is split into several smaller pieces to enable easier handling of the single segments. Using optical segmentation patterns enables pre-segmentation of the lens 69 into smaller pieces more reliably and with better control than prior ultrasonic techniques. Exemplary optical segmentation patterns are shown in FIG. 6A to 6C, as seen from the front of the lens 69. Depending on its hardness, lens 69 may be split into a variable number of segments, the number of segments typically, but not always, increasing with hardness. In the pattern of FIG. 6A, the optical beam 6 is scanned in a pattern of two crossing cuts 520, will is ideal for cataract grades 1-3 in order to split lens 69 into four sections, or quadrants. For cataracts of grade 3+ and higher, a scanned pattern as shown in FIG. 6B having three crossing cuts 522 to form sextants is ideal. For the hardest cataracts of grade 4-4+, a scanned pattern of four crossing cuts 524 implementing octant splitting as shown in FIG. 6C would be ideal.

Figure 7:
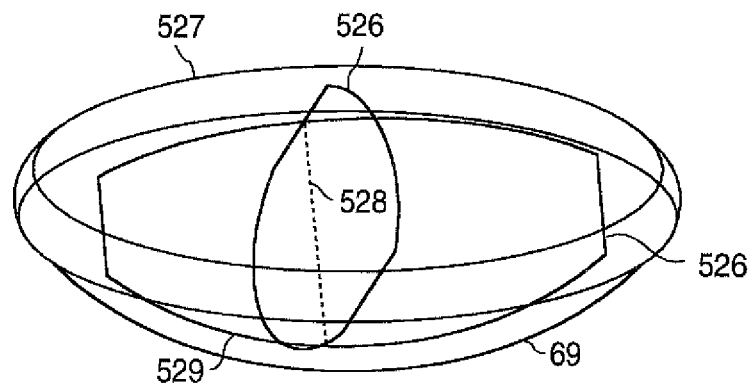
FIG. 7 is a perspective three-dimensional view of the eye lens illustrating inclined plane cuts within the lens.

System 2 can also be configured to laterally shift the center point of the splitting patterns of FIG. 6A to 6C over depth, creating inclined planes of laser induced damage via beam 6. This is shown in FIG. 7, where the two laser cut planes 526 shift their crossing point 528 throughout the depth of lens 69. This enables three dimensional inclined plane cuts within the lens 69 that promote easier removal of the quadrants from the anterior side 527 of the lens 69, as the problem of interference of the posterior edges 529 is avoided. Furthermore, the same benefits apply to the general case of any number of multiple axisymmetric intersecting cuts within the lens 69.

Figure 8A:
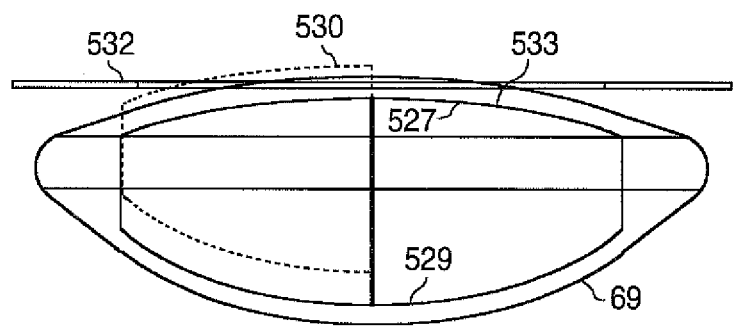
FIG. 8A is a side view of the eye lens illustrating non-inclined plane cuts within the lens.
Figure 8B:
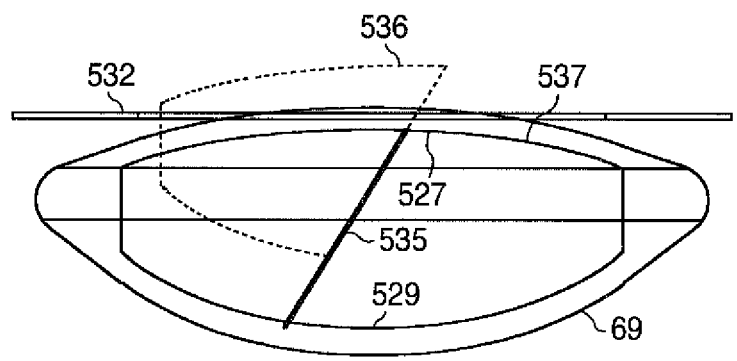
FIG. 8B is a side view of the eye lens illustrating inclined plane cuts within the lens.

The difficulty of extracting lens segments 530 through the limiting aperture of the iris 532 without an inclined plane is depicted in FIG. 8A. Without the ability to move laterally, the lens segment 530 will be blocked by the iris 532 due to anterior 527 and posterior 529 interference with the remaining lens segments 533. FIG. 8B is a side view of the inclined plane cuts described in FIG. 7. The inclined plane segment 536 can be removed through the iris 532 by sliding along the contact plane 535 with the remaining inclined plane lens segments 537.

Figure 9:
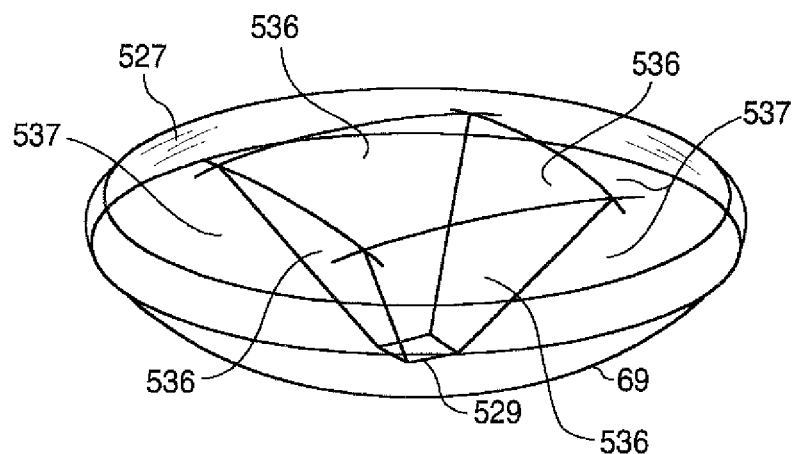
FIG. 9 is a perspective three-dimensional view of the eye lens illustrating inclined plane cuts within the lens forming a pyramid-shaped lens segment.

Another embodiment of lens segmentation is shown in FIG. 9 which consists of four inclined laser cut planes 536 merging in a manner to create a segment within lens 69 that is shaped similar to an inverted pyramid. This segment has its anterior portion 527 larger than its posterior portion 529, thus allowing it to be more easily removed. This simplifies the removal of the remaining lens sections 537 which allows faster progress of the surgeon. Furthermore, the same benefits apply to the general case of any number of multiple axisymmetric intersecting cuts inclined in the same manner within the lens 69.

Figure 10:
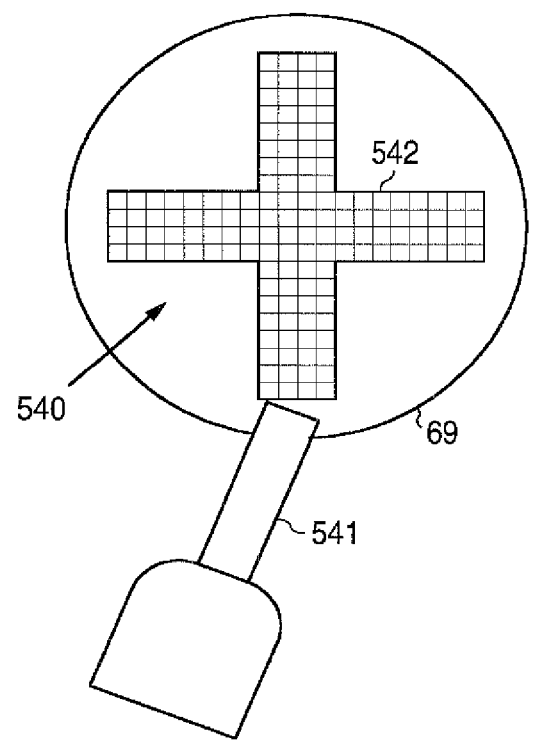
FIG. 10 is a top view of an eye lens illustrating a cross-shaped segmentation pattern.

FIG. 10 illustrates a cross-shaped optical segmentation pattern 540 which includes four cross bar quadrants 542. This pattern enables pre-formed channels which are used in the "divide and conquer" technique of phacoemulsification. This also allows easier splitting of the lens with phacoemulsification by direct mechanical means. The width of the cross bar quadrants 542 is preferably selected to correspond to the outer width of the phacoemulsification tip 541 used by the surgeon. A typically but not limiting example of tip widths includes 0.5 mm to 1.5 mm. The small quadrant width can be chosen to be smaller than the inner diameter of the phacoemulsification tip 541, such as between 0.3 mm and 1.3 mm, for easier insertion of the tip and aspiration of lens material.

Figure 11A:
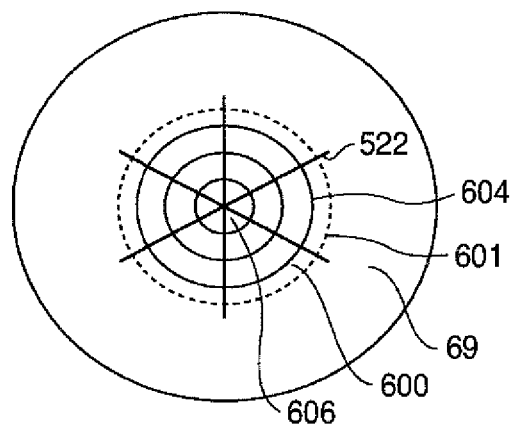
FIGS. 11A-11B are top views of an eye lens illustrating different configurations of a combination of linear and circular cuts.

FIG. 11A illustrates another optical segmentation pattern similar to that of FIGS. 5 & 6, which is especially useful in conditioning harder lens nuclei. FIG. 11A illustrates an optical segmentation pattern similar to that of FIG. 6B, but with the addition of concentric circular scans/cuts 604 that serve to further divide the nucleus 600 of lens 69 into segments small enough to be aspirated through a small probe and commensurately small capsular incision. In this example, the crossed cuts 522 extend beyond the nucleus 600 of lens 69, passing through nuclear boundary 601, and extending into the softer cortex and/or epi-nucleus of lens 69 that are inherently easy to remove via aspiration alone. Thus, by extending the laser segmentation pattern into the softer material surrounding nucleus 600, lens removal is further facilitated. The boundary 601 between nucleus 600 and the epi-nucleus or cortex of lens 69 may be determined via OCT device 100, and/or imaging system 71 by mapping the target tissues and discerning changes in the optical properties of the tissue. More opaque material will be readily apparent to both imaging system 71 and OCT device 100. The spatial map of their responses may be used by CPU 300 to generate a boundary for nucleus 600, and guide the patterning to include all of nucleus 600 and the peripheral softer material.

Figure 11B:
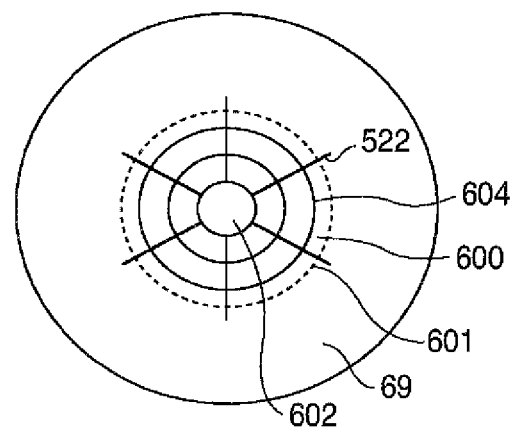

FIG. 11B shows an optical segmentation pattern similar to that of FIG. 11A, except that crossed cuts 522 do not pass through nucleus center 602, as it's already small enough to be easily aspirated. This may save time and cumulative energy delivered during a procedure, making it safer and more efficient.

Figure 12:
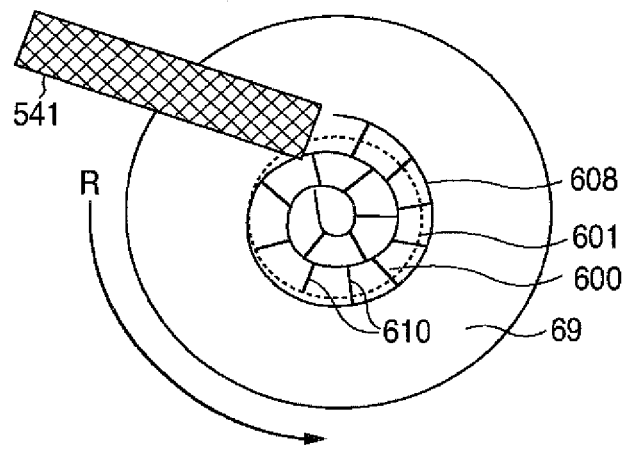
FIG. 12 is a top view of an eye lens illustrating a spiral shaped cut.

FIG. 12 shows an alternate optical segmentation pattern in the form of a "carousel pattern." The spiral shaped cut 608 of the "carousel" pattern allows for the increased ease of aspiration by causing the hardened nucleus 600 of lens 69 to unroll when aspirated by phacoemulsification tip 541, as indicated by direction R. The spiral spacing of the carousel pattern may be chosen to fit easily within phacoemulsification tip 541. Should the nucleus 600 be too stiff to easily unfurl along the spiral cut 608 of the carousel pattern, a series of sub-segment cuts 610 may be employed to cause the hardened nucleus to break into segments small enough to be easily aspirated by phacoemulsification tip 541. The width of a single section should be made to be smaller than the inner-diameter of the phacoemulsification tip 541, typically but not limited to inner-diameters between 1.1 mm and 0.25 mm. Alternate, orthogonal planes may also be cut into lens 69 to create smaller still segments of nucleus 600 to assist with its removal, especially with very hard nuclei.

Figure 13:
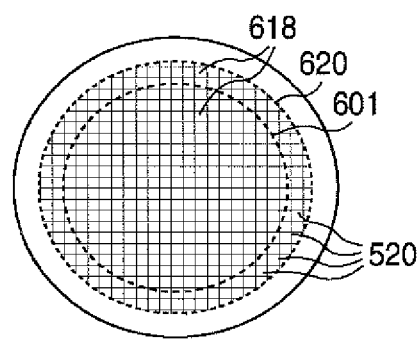
FIG. 13 is a top view of an eye lens illustrating an array of rectangular planar cuts.

FIG. 13 shows an alternate optical segmentation pattern, with an array of rectangular planar cuts 520 (i.e. crossing array of rows and columns of cuts) creating pattern 620 to facilitate removal of lens 69 by segmenting it into rectangular sub-elements 618. This is shown as extending beyond the boundary 601 of the nucleus 600 (not explicitly shown). As described above with respect to FIGS. 11 A and B, the width of a single section 618 should be made to be smaller than the inner-diameter of the phacoemulsification tip 541, typically but not limited to inner-diameters between 1.1 mm and 0.25 mm. Orthogonal planes (i.e. cuts parallel to the anterior surface 512 of the capsule) may also be cut into lens 69 to create smaller still segments and further assist with lens removal, especially with very hard nuclei.

Figure 14:
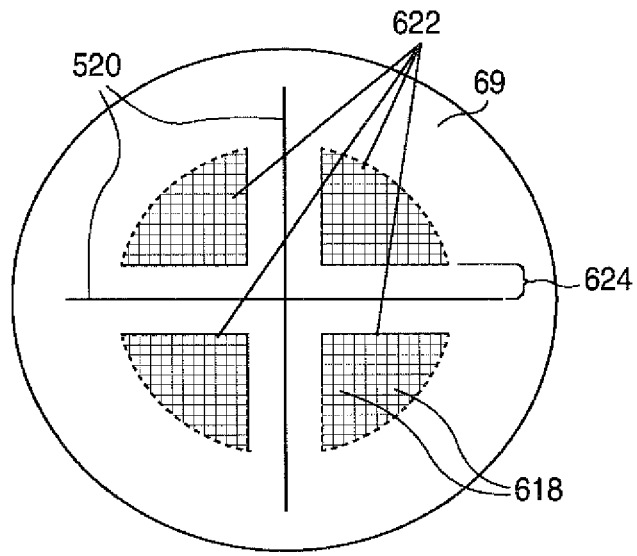
FIG. 14 is a top view of an eye lens illustrating segmentation into quadrants.

FIG. 14 depicts lens segmentation into quadrants 622 by creating planar crossed cuts 520 in the lens 69, together with softening cuts 618 within each quadrant to better facilitate removal of the lens by phacoemulsification. This technique combines segmenting cuts 520 that are larger (i.e. deeper, longer and/or generated with greater pulse energy), with softening cuts 618 that are smaller (shallower, shorter and/or generated with less pulse energy). The distance between the splitting and softening cuts are selected based on the hardness of the lens. The central plane cuts 520 allow the lens splitting forces to penetrate all the way out to the lens cortex, better assuring the reliable propagation of cracks along cuts 520. The spacing 624 between the splitting cuts 520 and the softening pattern of cuts 618 may be variable, but is typically but not limited to be between 0.1 mm to 1 mm.

Figure 15:
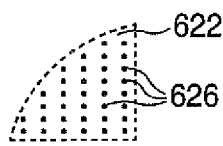
FIG. 15 is a top view of an eye lens illustrating softening cuts made into a lens quadrant.

FIG. 15 shows an another example of softening cuts, where each quadrant 622 is filled with a regular array of single laser spots 626 that are distributed throughout quadrant 622. Single laser spots 626 serve to soften the material of the lens in order to facilitate its removal. The patterning of laser spots 626 need not be regular, as shown. It may be a randomized distribution of spots throughout the volume subtended by quadrant 622.

Figure 16:
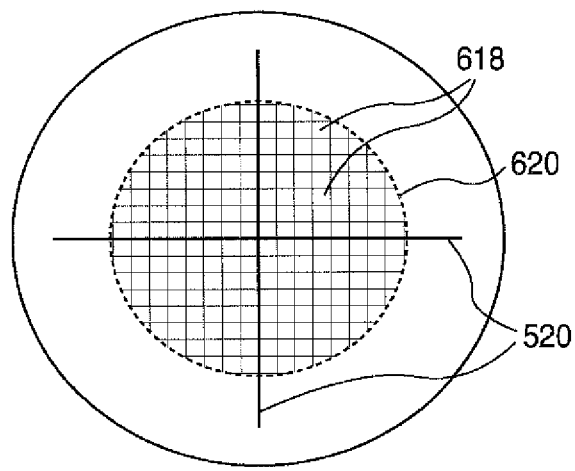
FIGS. 16-19 are top views of an eye lens illustrating various combinations of an array of rectangular planar cuts and one or more line cuts.

FIG. 16 depicts lens segmentation similar to that of FIGS. 13 & 14 with the addition of pattern 620 of softening cuts being confined to the center of the lens and segmenting cuts 520 being provided to facilitate the "bowl and chop" technique of phacoemsulification. The boundary of pattern 620 is shown as circular, but may be any shape. The central plane cuts 520 allow the lens splitting forces to penetrate all the way out to the lens cortex, better assuring the reliable propagation of cracks along cuts 520.

Figure 17:
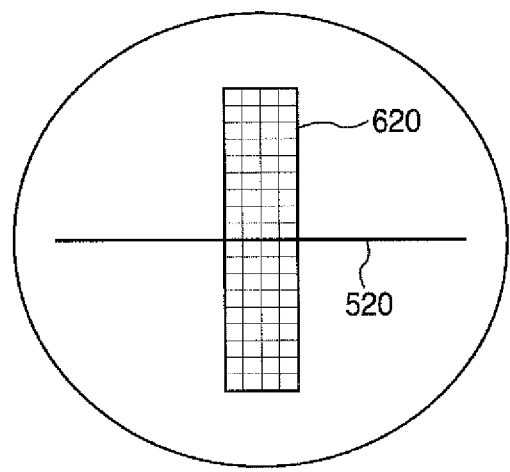
Figure 18:
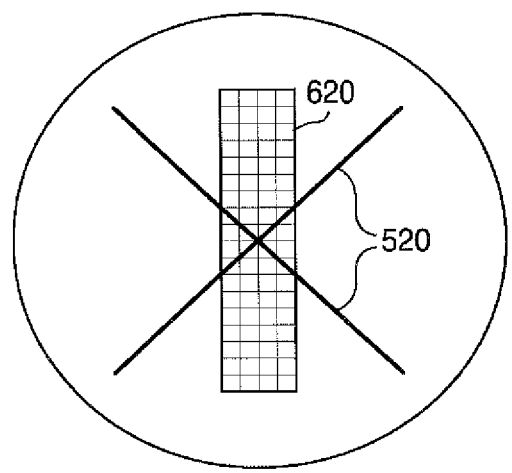

FIGS. 17 & 18 depict similar patterns to facilitate the "stop and chop" technique of phacoemsulification. The thickness of pattern 620 may be variable, but is typically but not limited to be between 0.1 mm to 1 mm. The central plane cuts 520 allow the lens splitting forces to penetrate all the way out to the lens cortex, better assuring the reliable propagation of cracks along cuts 520.

Figure 19:
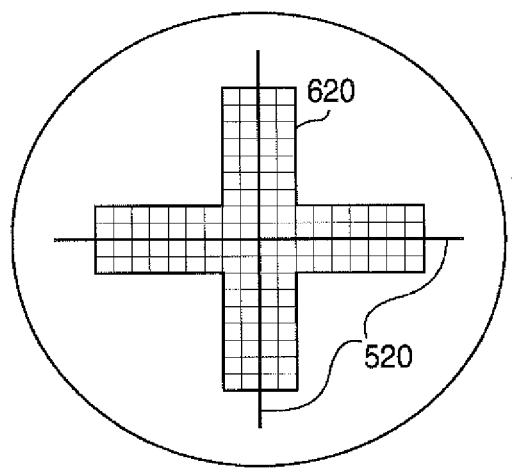

FIG. 19 depicts lens segmentation including central pattern 620 of softening cuts and segmenting cuts 520 to facilitate the combined "divide and conquer" and "prechopping" techniques of phacoemsulifcation. The meridonal thickness of pattern 620 may be variable, but is typically but not limited to be between 0.1 mm to 1 mm. The central plane cuts 520 allow the lens splitting forces to penetrate all the way out to the lens cortex, better assuring the reliable propagation of cracks along cuts 520.

For any pattern described above, the system 2 may also be made to deliver additional laser pulses or cuts to the incisions previously created in the lens material. These pulses can create bubbles that may serve to further separate the material for easier aspiration. Because it requires less energy density to cause a bubble to form at an interface, these later pulses can be attenuated as compared to the initial segmentation pulses. Furthermore, the laser beam may be made to linger at a location for a time sufficient to produce a large bubble, forcing the material to further separate. This can be done in a number of different ways. The system 2 may be configured to perform these separation pulses before, during and/or after a scan.

It is to be understood that the present invention is not limited to the embodiment(s) described above and illustrated herein, but encompasses any and all variations falling within the scope of the appended claims. For example, references to the present invention herein are not intended to limit the scope of any claim or claim term, but instead merely make reference to one or more features that may be covered by one or more of the claims. All the optical elements downstream of scanner 50 shown in FIGS. 1, 3 and 4 form a delivery system of optical elements for delivering the beam 6, 114 and 202 to the target tissue. Conceivably, depending on the desired features of the system, some or even most of the depicted optical elements could be omitted in a delivery system that still reliably delivers the scanned beams to the target tissue. Any softening pattern described above can instead be a segmenting pattern, where the lens pieces are segmented into even smaller pieces.

What is claimed is:

1. A method of treating a cataractous lens of a patient's eye, comprising:
   a. generating a light beam;
   b. deflecting the light beam using a scanner to form a treatment pattern of the light beam;
   c. delivering the treatment pattern to the lens of the patient's eye to create a plurality of cuts in the lens in the form two or more different incision patterns within the lens to segment the lens tissue into a plurality of patterned pieces, the incision patterns comprising:
   a first incision pattern comprising a plurality of laser incision planes each extending along a first length between a posterior and an anterior surface of the lens capsule, wherein the plurality of the incision planes of the first treatment pattern comprise at least two crossing cut incision planes, each crossing cut incision plane being a line segment when viewed en face; and
   a second incision pattern comprising one or more laser incisions, each extending along a first length between a posterior and an anterior surface of the lens capsule; and
   wherein a center point of each of the crossing cut incision planes is laterally shifted over a depth direction from the anterior surface to the posterior surface, thereby creating inclined incision planes, and an intersection of at least two of the crossing cut in planes is laterally shifted over the depth direction.

2. The method of claim 1, wherein the second incision pattern comprises one circle or two or more concentric circles.

3. The method of claim 2, wherein the second incision pattern comprises two or more concentric circles.

4. The method of claim 1, wherein the crossing cut incisions pass through the center of the lens as viewed from a posterior to an anterior position along the optical axis.

5. The method of claim 1, further comprising:
   a. deflecting the light beam using the scanner to form a softening treatment pattern of the light beam; and
   b. delivering the softening treatment pattern to the lens of the patient's eye to create a plurality of softening cuts that soften one or more portions of the lens before removal of the lens pieces from the patient's eye.

6. The method of claim 5, wherein the cuts formed by the treatment pattern are larger than the softening cuts formed by the softening treatment pattern.

7. The method of claim 1, wherein the two crossing cut incision planes are inclined planar incisions in the lens of the eye, each of which diverge away from an optical axis of the eye as viewed from a posterior to an anterior position along the optical axis.

8. The method of claim 7, wherein the two or more crossing cut incision planes are axisymmetric.

9. The method of claim 1, further comprising positioning an intraocular lens in the patient's lens capsule.

10. The method of claim 1, comprising incising an opening in an anterior surface of the lens capsule.

11. A method of treating a cataractous lens of a patient's eye, comprising:
    a. generating a light beam;
    b. deflecting the light beam using a scanner to form a treatment pattern of the light beam;
    c. delivering the treatment pattern to the lens of the patient's eye to create a plurality of cuts in the lens in the form two or more different incision patterns within the lens to segment the lens tissue into a plurality of patterned pieces, the incision patterns comprising:
    a first incision pattern comprising a plurality of laser incision planes each extending along a first length between a posterior and an anterior surface of the lens capsule wherein the plurality of the incision planes of the first treatment pattern comprise at least three crossing cut incision planes, each crossing cut incision plane being a line segment when viewed en face, and a second incision pattern comprising one or more laser incisions, each extending along a first length between a posterior and an anterior surface of the lens capsule; and wherein a center point of each of the crossing cut incision planes is laterally shifted over a depth direction from the anterior surface to the posterior surface, thereby creating inclined incision planes, and an intersection of at least two of the crossing cut in planes is laterally shifted over the depth direction.

12. The method of claim 11, wherein the second incision pattern comprises one circle or two or more concentric circles.

13. The method of claim 11, wherein the second incision pattern comprises two or more concentric circles.

14. The method of claim 11, wherein the crossing cut incisions pass through the center of the lens as viewed from a posterior to an anterior position along the optical axis.

15. The method of claim 11, further comprising:
 a. deflecting the light beam using the scanner to form a softening treatment pattern of the light beam; and
 b. delivering the softening treatment pattern to the lens of the patient's eye to create a plurality of softening cuts that soften one or more portions of the lens before removal of the lens pieces from the patient's eye.

16. The method of claim 15, wherein the cuts formed by the treatment pattern are larger than the softening cuts formed by the softening treatment pattern.

* * * * *